US011213462B2

(12) United States Patent
Clayton et al.

(10) Patent No.: US 11,213,462 B2
(45) Date of Patent: Jan. 4, 2022

(54) DENTAL ADHESIVE COMPOSITIONS

(71) Applicant: SDI (North America), Inc., Itasca, IL (US)

(72) Inventors: Tony Clayton, Bayswater (AU); Paul Farrar, Bayswater (AU); Manon Agrissais, Bayswater (AU)

(73) Assignee: SDI (NORTH AMERICA), INC., Itasca, IL (US)

( * ) Notice: Subject to any disclaimer, the term of this patent is extended or adjusted under 35 U.S.C. 154(b) by 112 days.

(21) Appl. No.: 16/088,073

(22) PCT Filed: Mar. 22, 2017

(86) PCT No.: PCT/AU2017/000069
§ 371 (c)(1),
(2) Date: Aug. 17, 2020

(87) PCT Pub. No.: WO2017/161408
PCT Pub. Date: Sep. 28, 2017

(65) Prior Publication Data
US 2020/0405584 A1 Dec. 31, 2020

(30) Foreign Application Priority Data
Mar. 24, 2016 (AU) ................ 2016901119

(51) Int. Cl.
*A61K 6/30* (2020.01)
*C08L 33/10* (2006.01)

(52) U.S. Cl.
CPC ............ *A61K 6/30* (2020.01); *C08L 33/10* (2013.01)

(58) Field of Classification Search
None
See application file for complete search history.

(56) References Cited

U.S. PATENT DOCUMENTS

| 4,588,756 | A | 5/1986 | Bowen |
| 5,321,054 | A | 6/1994 | Pasini |
| 10,641,688 | B2 * | 5/2020 | Wheeler ............... G01N 1/30 |
| 2004/0266906 | A1 | 12/2004 | Klee et al. |
| 2013/0045465 | A1 * | 2/2013 | Qian .................. A61K 6/30 433/217.1 |
| 2013/0217800 | A1 * | 8/2013 | Suh .................... A61K 6/30 522/30 |
| 2020/0405584 | A1 * | 12/2020 | Clayton ............... C08L 33/10 |

FOREIGN PATENT DOCUMENTS

| CN | 101035500 A | 9/2007 |
| CN | 101239024 A | 8/2008 |
| WO | 2003035013 A1 | 5/2003 |
| WO | 2007041587 A2 | 4/2007 |

OTHER PUBLICATIONS

Google scholar key word search (Year: 2021).*
ip.com search of the PG pub (Year: 2021).*
Chinese Office Action with English translation for corresponding Chinese Application No. 2018-549880, dated Jan. 10, 2021, 7 pages.
International Search Report for corresponding International Application No. PCT/AU2017/000069, dated May 26, 2017, 5 pages.
Written Opinion for corresponding International Application No. PCT/AU2017/000069, dated May 26, 2017, 3 pages.
European Office Action for corresponding European Application No. 17 769 177.1, dated May 25, 2021, 4 pages.
European Search Report for corresponding European Application No. 17 769 177.1, dated Oct. 24, 2019, 5 pages.
English Language Summary of Second Chinese Office Action for corresponding Chinese Application No. 2018-549880, undated, 1 page.

* cited by examiner

*Primary Examiner* — Peter A Salamon
(74) *Attorney, Agent, or Firm* — Reising Ethington P.C.

(57) ABSTRACT

A dental adhesive composition, having a solvent which is an azeotrope of methyl ethyl ketone with water. Optionally, the azeotropic solvent may comprise in addition, ethanol or isopropanol. The boiling point of the solvent is less than 75° C.

8 Claims, No Drawings

DENTAL ADHESIVE COMPOSITIONS

FIELD OF THE INVENTION

The present invention relates to dental adhesive compositions.

BACKGROUND

Dental adhesive compositions typically contain a range of components such as adhesion-promoting monomers, hydrophilic monomers, hydrophobic monomers, stabilisers, photo-initiators and co-initiators. These components and other suitable additives are known to those skilled in the art. These components are dissolved in a solvent.

Adhesion-promoting monomers typically possess a structure containing an acidic functionality (e.g. carboxylic, phosphoric, phosphonic, or sulfonic) and a polymerisable functional group, such as acrylate or methacrylate. Common examples of these monomers used in dental adhesives are 10-methacryloxydecyl dihydrogen phosphate (MDP) and 4-methacryloxyethyl trimellitic acid (4-MET).

Hydrophilic monomers possess mono- or multi-polymerisable functionality and are substantially miscible with water. They are generally incorporated in adhesive formulations to help compatibilise the more hydrophobic components with water. Common examples of these hydrophilic monomers are HEMA, glycerol dimethacrylate (GDMA) and hydroxypropyl methacrylate (HPMA).

Hydrophobic monomers typically possess mono- or multi-polymerisable functionality, but are substantially immiscible with water. They are generally added to provide strength and water-resistance to a cured adhesive. Common examples of these hydrophobic monomers are bisphenol A glycidylmethacrylate (BisGMA), urethane dimethacrylate (UDMA) and ethoxylated bisphenol A dimethacrylate (BisEMA).

Photo-initiators, optionally combined with co-initiators, may be added to provide adhesive formulations with the ability to cure upon exposure to an appropriate light source. Common photo-initiators used in dental adhesives are camphorquinone (CQ) and diphenyl (2,4,6-trimethylbenzoyl) phosphine oxide (TPO). Co-initiators, such as ethyl 4-dimethylaminobenzoate (EDMAB) and dimethylaminoethyl methacrylate (DMAEMA), may be used to improve the reaction speed of some photo-initiator systems.

Stabilisers may be added to adhesive formulations to prevent premature polymerisation. Typically, the stabilisers are free-radical scavengers such as butylated hydroxytoluene (GHT), monomethyl ether of hydroquinone (MEHQ) or hydroquinone (HQ).

Organic solvents such as ethanol and acetone are typically incorporated in dental adhesive compositions to (1) reduce viscosity, (2) compatibilise resin ingredients with water, (3) improve surface wetting and (4) increase depth of penetration into dental tissues. Typically, the solvents also contain water. A substantial percentage of water is required in the final adhesive formulation to achieve a thorough wetting of the moist dentin.

Ideally, after serving these purposes, all solvents (including water) should be removed since residual solvents will only weaken a final cured adhesive layer, which is the foundation layer of good bonding between a tooth and a subsequent restorative material such as a composite, a glass ionomer cement or an amalgam. Poor bonding can result in marginal deterioration, leading to marginal staining and development of caries.

In general, solvent-containing adhesives have a solvent-removal step after application which involves air-blowing the applied layer for a period of time.

Solvents removed during this step typically include both organic solvents and water. Ethanol-solvated compositions will typically dry as an azeotrope of 96% ethanol and 4% water which, depending on the initial ethanol-water ratio, often leads to a high level of residual water, thus weakening the adhesive layer. On the other hand, ethanol is good for storage stability.

Acetone-containing compositions lose acetone quite readily upon air-blowing. However, due to absence of an acetone-water azeotrope, the water removal is again problematic, thus resulting in high levels of residual water.

Acetone-containing compositions are also difficult to store due to the high volatility of acetone. Bottles and containers readily lose acetone solvents causing the adhesive to become viscous and, in some cases, phase-separated.

SUMMARY OF THE INVENTION

It would be advantageous to have a solvent system that exhibits a good evaporation rate of organic solvent and water during air-blowing, whilst possessing reduced loss of volatiles upon storage.

In accordance with one aspect of the present invention there is provided a dental adhesive composition comprising an organic solvent component which contains methyl ethyl ketone. Preferably, the solvent also contains water.

It has been found that methyl ethyl ketone is able to form an azeotrope with water. The azeotrope has a lower boiling point and higher percentage water removal compared to a water/ethanol azeotrope. Preferably the methyl ethyl ketone is dissolved in water either alone or in conjunction with an alcohol such as ethanol or isopropanol.

Preferably the solvent has a boiling point in the range from 60° to 100° C. More preferably the solvent has a boiling point of less than 75° C. Still more preferably the solvent may have a boiling point in a range from 70° to 74° C.

DESCRIPTION OF THE PREFERRED EMBODIMENTS

Examples of solvent systems used in the present invention are as follows: Preferably the dental adhesive composition of the present invention contains:

a) From 15%-60% by weight of total organic solvent;

b) From 0.5%-20% by weight of water;

c) From 40%-90% by weight of light curable adhesive monomer mixture.

Examples of solvent systems used in the present invention are as follows:

Example 1

The solvent may comprise a binary mixture of methyl ethyl ketone and organic alcohol and water or a ternary system which is a mixture of methyl ethyl ketone and water and organic alcohol which is isopropanol alcohol or ethanol.

TABLE 1

Solvent systems for dental adhesive formulation and their characteristics

| | 1st Solvent % in azeotrope [boiling point] | 2nd Solvent % in azeotrope [boiling point] | 3rd Solvent % in azeotrope [boiling point] | Azeotrope boiling point |
|---|---|---|---|---|
| (a) Water/Ethanol/MEK | Water 11% [100° C.] | Ethanol 14% [78.4° C.] | MEK 75% [79.6° C.] | 73.2° C. |
| (b) Water/Isopropanol/MEK | Water 11% [100° C.] | Iso-propanol 1% [82.5° C.] | MEK 88% [79.6° C.] | 73.4° C. |
| (c) Water/MEK | Water 11% [100° C.] | — | MEK 89% [79.6° C.] | 73.5° C. |
| Water/Ethanol | Water 4.5% [100° C.] | Ethanol 95.5% [78.4° C.] | — | 78.1° C. |
| Water/Isopropanol | Water 12.1% [100° C.] | Iso-propanol 87.9% [82.5° C.] | — | 80.4° C. |
| Water/Acetone | Water (No azeotrope) [100° C.] | Acetone (No azeotrope) [56.5° C.] | — | No azeotrope |

The examples above in Table 1 include ternary solvent systems a and b and a binary solvent system c. In each case the solvent contains a substantial amount of water but has a boiling point below 75° C. As shown in the Table, it is found that other azeotropic solvent systems such as water/ethanol and water/iso-propanol have higher boiling points than the items mentioned above. Also, the systems described above and according to the present invention have better storage stability and are less volatile then a water/acetone system.

The methyl ethyl ketone based azeotropes according to the present invention have a good combination of high water content, meaning a high-water removal rate and moderate boiling point. The benefit of the moderate boiling point is good storage stability whilst still exhibiting an acceptable evaporation rate during air-blowing.

The methyl ethyl ketone based azeotropes according to the present invention provide clear benefits over ethanol based azeotropes including lower boiling points and higher water removal rates.

Example 2

TABLE 2

Solvent Mixes

| | Mix | | | |
|---|---|---|---|---|
| | 1 | 2 | 3 | 4 |
| Solvent System | Acetone/Water | MEK/Water | MEK/Ethanol/Water | Ethanol/Water |
| % weight | 70/30 | 89/11 | 75/14/11 | 70/30 |

Solvent mixes presented in table 2 were prepared and stored in high density polyethylene (HDPE) black bottles at 35° C. The bottles, with an internal volume of 6 ml and wall thickness of 0.8 μm in average, were partially filled with the solvent mixes. The bottles were closed with HDPE tip and cap and initially weighed. Solvent loss was evaluated by weighing the bottles periodically. Calculation of the percentage of solvent lost compared to the initial amount is made. The relative solvent loss trend between the systems was same over the testing period (80 days).

The solvent loss of the solvent systems (1) Acetone/Water; (2) MEK/Water; (3) MEK/Ethanol/Water is superior to (4) Ethanol/Water The results show that from the point of view of solvent loss through HDPE bottles, the Ethanol/Water solvent system is the most stable, likely to be due to the higher boiling point of the mixture.

Example 3—Combination of Solvent Mixes and Adhesive Resin

Examples of solvent systems used in the present invention are as follows:

Adhesive formulations were prepared by combining solvent mixes and adhesive resin with a 1:1 weight ratio. Mixing was carried out under yellow light.

Resulting formulations are provided as illustrations of further possible formulations.

TABLE 3

Adhesive Resin Formulation

| Component | % (weight) |
|---|---|
| Urethane Dimethacrylate | 11 |
| Triethylene Glycol Dimethacrylate | 15 |
| Adhesive Monomers | 15.9 |
| Camphorquinone + Ethyl-4-(dimethylamino)benzoate | 3 |
| Butylated hydroxytoluene | 0.1 |
| Pyrogenic Silica | 5 |
| Sodium Fluoride | 0.1 |
| Solvent Mix | 50 |

Combining the above resin formulation and the solvent mixes of Example 1, four adhesive formulations were prepared. The final solutions were stored in 6 ml HDPE Black bottles closed by HDPE black tip and cap.

Example 4—Evaporation

One drop of the adhesive formulations mentioned above was applied to the surface of a flat glass slide placed undisturbed on a scale at room temperature. The evaporation was evaluated by recording the weight every 30 seconds over 5 minutes. Calculation of the percentage of the mass lost compared to initial was made.

TABLE 4

Evaporation of Adhesive Formulations with Various Solvent Systems

|  | Mix | | | |
|---|---|---|---|---|
|  | 1 | 2 | 3 | 4 |
| Solvent System | Acetone/Water | MEK/Water | MEK/Ethanol/Water | Ethanol/Water |
| % in total formulation | 35/15 | 44.5/5.5 | 37.5/7/5.5 | 35/15 |
| % mass lost at 1 min | 10 | 17 | 34 | 10 |
| % mass lost at 5 min | 24 | 37 | 43 | 38 |
| % solvent remaining after 5 min | 26 | 13 | 7 | 12 |

The results show that the solvent mix 3 performs better in terms of solvent removal rate and residual solvent. The azeotrope also ensures a high-water removal rate along with the organic solvent.

Example 5—Phase Separation (after Drying)

One drop of each of the adhesive formulations mentioned above was applied to the surface of a flat glass slide placed undisturbed at room temperature.

Phase separation during evaporation was assessed visually by assessing the haziness of the drop straight after deposition and after 5 minutes.

Separation of the insoluble organic resin from the water phase—meaning unhomogeneity of the solution—is translated by obvious haziness of the droplet.

TABLE 5

Phase Separation of Adhesive Formulations with Various Solvent Systems

|  | Mix | | | |
|---|---|---|---|---|
|  | 1 | 2 | 3 | 4 |
| Solvent | Acetone/Water | MEK/Water | MEK/Ethanol/Water | Ethanol/Water |
| Initial phase separation? | Yes All drop hazy | No | No | No |
| Phase separation at 1 min? | Yes All drop hazy | No | No | Yes All drop hazy |
| Phase separation at 5 min? | Yes All drop hazy | No | No | Yes Edges hazy |

The results show that only MEK-containing mixtures give homogeneous adhesive formulation and prevent phase separation.

Example 6—Summary of Solvent System Characteristics

TABLE 6

Summary of the Examples

|  | Mix | | | |
|---|---|---|---|---|
|  | 1 | 2 | 3 | 4 |
| Solvent | Acetone/Water | MEK/Water | MEK/Ethanol/Water | Ethanol/Water |
| Solvent loss (storage bottle) | ✓ | ✓ | ✓ | ✓✓ |
| Solvent evaporation/water removal | xx | ✓ | ✓✓ | x |
| Resistance to phase separation | xx | ✓ | ✓ | x |

As shown in Table 6, using MEK-based azeotrope solvent systems gives substantial benefits to adhesive formulation, without being detrimental to packaging stability.

Example 7—Bonding Performance

In order to assess the benefit of the ternary solvent system over the binary Ethanol/Water solvent system that have better storage stability, the shear bond strength to human dentin was evaluated initially and after one month of storage in deionised water.

Caries-free, restoration-free human teeth (recently extracted, stored (<3 months) in Chloramine B) were sectioned (diamond-blade saw) perpendicularly to this occlusal surface. The teeth were embedded in epoxy resin and wet-ground to 600-grit with Silicon Carbide paper.

Adhesives were applied to dentin then attached to an Ultradent Jig (d=2.4 mm) before light-curing for 10 seconds at 1,500 mW·cm-2. An A2 shade composite was condensed into mold and light-cured for 20 seconds. After 15 min in humidor at 37° C. specimens were demounted.

Half of the specimens were stored at 37° C. during 24 h before Shear Bond Strength testing (0.75 mm·min-1/INSTRON-5942). The other half was stored for one (1) month at 37° C. in deionised water—changed weekly—before testing.

The shear bond strength and standard deviation values are presented in the table below. Means with same letter are not significantly different (p<0.05).

TABLE 7

Shear Bond Strength of MEK-based formulations

|  | Mix | |
|---|---|---|
|  | 3 | 4 |
| Solvent | MEK/Ethanol/Water | Ethanol/Water |
| Shear Bond Strength | | |
| 24 h (MPa) | 23.9 (5.1)[a] | 19.5 (4.6)[a,b] |
| 1 month (MPa) | 22.5 (3.5)[a] | 17.2 (5.9)[b] |
| % drop | 6 | 12 |

As shown in Table 7, shear bond strength to human dentin is initially higher with the ternary MEK-azeotrope solvent system. Moreover, the drop after one month storage in water is half the drop exhibited by the binary Ethanol/Water solvent system.

The invention claimed is:

1. A dental adhesive composition characterised by comprising a solvent which is an azeotrope of methyl ethyl ketone with water.

2. A dental adhesive composition according to claim 1 in which the solvent is a binary azeotropic system comprising methyl ethyl ketone and water.

3. A dental adhesive composition according to claim 1, characterised in that said solvent is a ternary azeotrope solvent system comprising methyl ethyl ketone and water together with an organic alcohol.

4. A dental adhesive composition according to claim 3, characterised in that said organic alcohol is ethanol or isopropanol.

5. A dental adhesive composition according to claim 1 characterised in that said solvent has a boiling point of less than 75° C.

6. A dental adhesive composition according to claim 5, characterised in that said solvent has a boiling point in the range from 70-74° C.

7. A dental adhesive composition according to claim 1 characterised in that said composition comprises 15-60% by weight of organic solvent, 0.5-20% by weight of water and 40-90% by weight of light curable adhesive monomer.

8. A dental adhesive composition characterised by comprising a solvent which is an azeotrope of methyl ethyl ketone with water; said solvent is a ternary azeotrope solvent system comprising methyl ethyl ketone and water together with an organic alcohol; said solvent has a boiling point in the range from 70-74° C.; said composition comprises 15-60% by weight of organic solvent, 0.5-20% by weight of water and 40-90% by weight of light curable adhesive monomer.

* * * * *